(12) United States Patent
Litkowski et al.

(10) Patent No.: US 6,338,751 B1
(45) Date of Patent: *Jan. 15, 2002

(54) COMPOSITIONS CONTAINING BIOACTIVE GLASS AND THEIR USE IN TREATING TOOTH HYPERSENSITIVITY

(75) Inventors: Leonard J. Litkowski, Baltimore; Gary D. Hack, Columbia, both of MD (US); David C. Greenspan, Gainesville, FL (US)

(73) Assignees: USBiomaterials Corp, Alachua, FL (US); University of Maryland, Baltimore, Baltimore, MD (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/052,647

(22) Filed: Mar. 31, 1998

Related U.S. Application Data

(63) Continuation of application No. 08/895,329, filed on Jul. 16, 1997, now Pat. No. 5,735,942, which is a continuation of application No. 08/597,936, filed on Feb. 7, 1996, now abandoned.

(51) Int. Cl.[7] .......................... C03C 3/097; A61K 7/16
(52) U.S. Cl. ............................. 106/35; 501/57; 501/58; 501/63; 424/49; 424/52; 424/57; 433/226
(58) Field of Search .............................. 106/35; 501/24, 501/25, 57, 58, 63, 72; 424/49, 52, 57; 433/226

(56) References Cited

U.S. PATENT DOCUMENTS

| | | |
|---|---|---|
| 3,981,736 A | 9/1976 | Broemer et al. |
| 4,057,621 A | 11/1977 | Pashley et al. |
| 4,239,113 A | 12/1980 | Gross et al. |
| 4,538,990 A | 9/1985 | Pashley |
| 4,605,415 A | 8/1986 | Richez |
| 4,775,592 A | 10/1988 | Akahane et al. |
| 4,775,646 A | 10/1988 | Hench |
| 4,783,429 A | 11/1988 | Shibuya et al. |
| 4,851,046 A | 7/1989 | Low et al. |
| 4,920,082 A | 4/1990 | Danielson |

(List continued on next page.)

FOREIGN PATENT DOCUMENTS

| | | |
|---|---|---|
| WO | WO96/10985 | 4/1996 |
| WO | WO96/00536 | 11/1996 |
| WO | WO97/27148 | 7/1997 |
| WO | WO99/13852 | 3/1999 |

OTHER PUBLICATIONS

Hench, Larry L. and West, Jon K., "Biological Applications of Bioactive Glasses," *Life Chemistry Reports*, v.13, pp. 187–241, (1996).

*Primary Examiner*—Karl Group
(74) *Attorney, Agent, or Firm*—Burns, Doane, Swecker & Mathis, L.L.P.

(57) ABSTRACT

A novel silica based bioactive glass composition that can be used in conjunction with a delivery agent such as a toothpaste, gel saliva, etc. having a particle size range <90 µm which will form a rapid and continuous reaction with body fluids due to the immediate and long term ionic release of Ca and P from the core silica particles, to produce a stable crystalline hydroxy carbonate apatite layer deposited onto and into the dentin tubules for the immediate and long term reduction of dentin hypersensitivity.

2 Claims, 9 Drawing Sheets

U.S. PATENT DOCUMENTS

| | | |
|---|---|---|
| 5,037,639 A | 8/1991 | Tung |
| 5,120,340 A | 6/1992 | Ducheyne et al. |
| 5,204,106 A | 4/1993 | Schepers et al. |
| 5,236,458 A | 8/1993 | Ducheyne et al. |
| 5,268,167 A | 12/1993 | Tung |
| 5,296,026 A | 3/1994 | Monroe et al. |
| 5,314,474 A | 5/1994 | Helms et al. |
| 5,340,776 A * | 8/1994 | Paschke et al. ............... 501/11 |
| 5,356,951 A * | 10/1994 | Yearn et al. ................ 523/116 |
| 5,425,771 A | 6/1995 | Helms et al. |
| 5,427,768 A | 6/1995 | Tung |
| 5,429,996 A | 7/1995 | Kaneko |
| 5,432,130 A | 7/1995 | Rheinberger |
| 5,571,502 A | 11/1996 | Winston et al. |
| 5,603,922 A | 2/1997 | Winston et al. |
| 5,605,675 A | 2/1997 | Usen et al. |
| 5,614,175 A | 3/1997 | Winston et al. |
| 5,628,429 A | 5/1997 | Usen et al. |
| 5,641,347 A | 6/1997 | Grabrowski et al. |
| 5,645,853 A | 7/1997 | Winston et al. |
| 5,741,479 A * | 4/1998 | Masterman et al. .......... 106/35 |
| 5,766,328 A * | 6/1998 | Nakabayashi et al. ........ 106/35 |
| 5,817,296 A | 10/1998 | Winston et al. |
| 5,833,957 A | 11/1998 | Winston et al. |
| RE36,035 E | 1/1999 | Usen et al. |
| 5,858,333 A | 1/1999 | Winston et al. |
| 5,860,565 A | 1/1999 | Winston et al. |
| 5,866,102 A | 2/1999 | Winston et al. |
| 5,895,641 A | 4/1999 | Usen et al. |

* cited by examiner

COMPOSITIONS CONTAINING BIOACTIVE GLASS AND THEIR USE IN TREATING TOOTH HYPERSENSITIVITY

This application is a continuation of application Ser. No. 08/895,329, filed Jul. 16, 1997, now U.S. Pat. No. 5,735,942 which is a continuation of 08/597,936 filed Feb. 7, 1996, now abandoned.

FIELD OF THE INVENTION

The present invention relates to bioactive glass compositions. More particularly, the present invention relates to improved compositions of bioactive glass including particles having size ranges significantly lower than previous compositions. The present invention also relates to a method of treating tooth hypersensitivity.

BACKGROUND OF THE INVENTION

Tooth hypersensitivity is a common problem which affects about 40 million adults in the United States, 10 million of which can be considered chronically affected. Kanapka, *Dent. Clin. North Am.*, 34:54 (1990). It is estimated that some 17% of adults in the U.S. have at least one or more sensitive teeth. Hypersensitive teeth may be sensitive to cold, heat, air or sugary foods.

The incidence of tooth hypersensitivity increases with age. Tooth hypersensitivity is believed to be related to the general increase in exposed root surfaces of teeth as a result of periodontal disease, tooth brush abrasion, or cyclic loading fatigue of the thin enamel near the dento-enamel junction. When root surfaces are exposed, dentinal tubules are also exposed. Dentinal tubules are naturally present in the dentinal layer of the tooth and they provide for an osmotic flow between the inner pulp region of the tooth and the outer root surfaces.

The currently accepted theory for tooth hypersensitivity is the hydrodynamic theory. Greenchill and Pashley, *Journal of Dental Research*, Vol. 60, pp. 686–698 (1981). This theory is based on the belief that open exposed dentinal tubules allow fluid flow through the tubules. This flow excites the nerve endings in the dental pulp. Clinical replicas of sensitive teeth viewed in a scanning electron microscope (SEM) reveal varying numbers of open or partially occluded dentinal tubules. (See FIGS. 1 and 2).

Certain dental procedures may result in a weak smear layer of dentinal debris 2–5 microns in thickness that covers the tooth surface and masks the tubules. in vitro, this smear layer is a normally occurring artifact of sectioning or preparing the tooth structure. A smear layer is easily removed by brushing or by other acids naturally present in the mouth or foods. When a smear layer is present, the fluid flow that can occur through the dentin is only a few percent of that possible following acid removal of the smear layer, which opens and enlarges the tubules. Accordingly, it is necessary to remove any smear layer when experimenting with the efficacy of a tooth hypersensitivity treatment in order to simulate sensitive dentin.

There is a growing body of evidence that occlusion of the dentinal tubules of a sensitive tooth by resin infiltration, varnish coat, or crystallite precipitation results in reduction or elimination of the hypersensitivity. The duration of relief, however, is highly variable. Hypersensitivity usually reappears because of tooth brush abrasion, presence of acid challenges in the mouth, or degradation of the coating material.

For example, a two-step procedure involving application of a calcium nitrate solution and a potassium phosphate solution to the tooth has been found to produce numerous calcium phosphate crystals. Kaminske et al, *J. Dent., Res.*, 69:68 (1990).

Increasing concentrations of oxalic acid in the food bolus derived from dietary sources up to 1.14 g/l have also been found to yield precipitation of a deposit at the tooth surface. A maximal response was found to be obtained at a level of 0.1% (w/v) oxalic acid equivalents. Greater levels of oxalic acid did not yield greater protection of teeth. It has been postulated that the deposited material is calcium oxalate, resulting from interaction of the oxalic acid with calcium in the saliva. Gortner et al, *J. Nutr.*, 32:121 (1946). The level of calcium in saliva is very low, however, thus the treatment is not very successful.

Alkali metal or ammonium oxalate have also been used to reduce tooth hypersensitivity. The low pH of the solution is believed to mobilize calcium and phosphate from the hard tissues (U.S. Pat. No. 4,057,621).

In addition, a 3.0% (w/v) monohydrogen monopotassium oxalate solution has been found to occlude dentinal tubules. Pashley et al, *Arch. Oral. Biol.*, 23:1127 (1978). However, the treatment regimen deposits very few crystals on the dentin surface or within the tubules, and these deposited crystals are readily removed by water irrigation. Knight et al., *J. Periodontal*, 64:366–373 (1993).

Desensitizing dentifrices with potassium oxalate have been found to provide temporary tubule occlusion. Pashley et al., *J. Periodont.*, 55:522(1984). Potassium oxalate is thought to react with the smear layer to increase its resistance to acid attack as well as reduce its permeability. It is thought that the crystals produced when dentin is treated with potassium oxalate are calcium oxalate. Pashley et al, *Arch. Oral Biol.*, 30.731 (1985).

A two-component kit including a first 1.0–30% (w/v) neutral oxalate solution, such as dipotassium oxalate, and a second subsequent 0.5–3.0% (w/v) acidic oxalate solution, such as monopotassium-monohydrogen oxalate is described in U.S. Pat. No. 4,538,990. It is claimed that the neutral oxalate forms large crystals over the dentinal surface, and the acidic oxalate forms smaller crystals around and about the previously formed larger crystals to form a combined uniform layer of microscopic crystals.

Studies on the occlusion of dentinal tubules by deposition of crystals from potassium oxalate-based media (30% w/v $K_2C_2O_4$) have shown variable results, purportedly due to variations in the size and number of crystals generated by the two solutions. These variations in size and numbers of crystals may depend on such factors as the pH of the solutions. The rate of crystal formation is influenced by the local $Ca^{2+}$ ion concentration and the acidic 3.0% (w/v) solution of $KHC_2O_4$ generates an extremely high local calcium ion concentration by etching the tooth. As a result of the extremely high local calcium ion concentration, there is greatly accelerated formation of abundant crystals to yield the desired reduction in hypersensitivity. Muzzin et al, *J. Periodont.*, 60:151 (1989). However, the source of ionized calcium within the dentinal fluid is not explained and the extremely high local calcium ion concentration is not defined.

A widely used one-step method for occluding dentinal tubules, PROTECT™ (J. O. Butler, Chicago, Ill.), involves the application of a solution of $KHC_2O_4$ to the tooth surface. This solution does not contain calcium salts because it is believed that etching of tooth structure by the reagent contributes a more than adequate supply of $Ca^{2+}$ to enable sufficient precipitation and crystal formation when the compound is applied to the tooth surface or in the tubule.

All of the above referenced materials use biologically inactive inorganic or organic components that will occlude the open tubules for a limited time period. Normal habits including the eating of acidic foods and vigorous toothbrushing will remove the materials from the tubules allowing fluid flow and a recurrence of sensitivity. In addition, literature has demonstrated that simple rinsing with water significantly reduces the number of tubules occluded with many of the available anti-hypersensitivity agents. Knight et al, *Journal of Periodentology*, Vol. 64, pp. 366–373 (1993).

Bioactive and biocompatible glasses have been developed as bone replacement materials. Studies have shown that these glasses will induce or aid osteogenesis in a physiologic systems. Hench et al, *J. Biomed. Mater. Res.* 5:117–141 (1971). The bond developed between the bone and the glass has been demonstrated to be extremely strong and stable. Piotrowski et al., *J. Biomed. Mater. Res.* 9:47–61 (1975). Toxicology evaluation of the glasses has shown no toxic effects in bone or soft tissue in numerous in vitro and in vivo models. Wilson et al., *J. Biomed. Mater. Res.* 805–817 (1981). However, the glass has been reported to be bacteriostatic of bacteriocidal most likely related to the change in pH induced by the dissolution of the ions from the surface of the glass and lack of bacterial adherence to the glass surface. Stoor et al., Bioceramics Vol. 8 p. 253–258 Wilson et al (1995).

The bonding of the glass to bone begins with the exposure of the glass to aqueous solutions. $Na^+$ in the glass exchanges with H+ from the body fluids causing the pH to increase. Ca and P migrate from the glass forming a Ca—P rich surface layer. Underlying this Ca—P rich is a layer which becomes increasingly silica rich due to the loss of Na, Ca and P ions (U.S. Pat. No. 4,851,046).

The behavior of the bioactive glass as solid implants in a dental application was reported by Stanley et al., Journal of Prostetic Dentistry, Vol. 58, pp. 607–613 (1987). Replicate tooth forms were fabricated and implanted into extracted incisor sockets of adult baboons. Successful attachment of the implants to surrounding bone was seen after histologic examination at six months. Clinical application of this technique is presently available for human use. Endosseous Ridge Maintenance Implant ERM®. Particulate bioactive glass has been used for periodontal osseous defect repair (US Pat. No. 4,851,046) utilizing a size range of 90–710 $\mu$m and a compositional range described in the following chart.

| Component Weight | Percentage |
| --- | --- |
| $SiO_2$ | 40–52 |
| CaO | 10–30 |
| $Na_2O$ | 10–35 |
| $P_2O_5$ | 2–8 |
| $CaF_2$ | 0–25 |
| $B_2O_3$ | 0–10 |

Previously described data has shown that 60% silica is beyond the limit of bioactive melt derived glasses. Okasuki et al. Nippon Seramikbusu Kyokai Gakijutsu Konbuski, Vol. 99, pp. 1–6 (1991). The use of bioactive glasses for bonding to dentin has not been previously described. Moreover, these bioactive glasses are not suitable for treating tooth hypersensitivity.

Previously, bioactive glasses have been used only in larger size ranges and have only been applied to bone. The 90–710 $\mu$m size range was determined to be the most effective for periodontal applications when in direct contact with bone. However, size ranges smaller than 90 $\mu$m were ineffective due to their high rate of reactivity and rapid resorption at the bony site. Moreover, size ranges smaller than 90 $\mu$m were determined to be ineffective in soft tissue sites also due to the presumption that the smaller particles were removed by macrophages (see U.S. Pat. No. 4,851, 046). A size range of less than 200 $\mu$m was also found to be ineffective in certain bone defects (see U.S. Pat. No. 5,204, 106) due to the high rate of reactivity.

U.S. Pat. No. 4,239,113 ("the '113 patent") also describes the use of a bone cement. The '113 patent only discloses bioactive glass ceramic powder having a particle size of 10–200 microns. Moreover, the '113 patent also requires the use of methylmethacrylate (co)polymers and vitreous mineral fibers.

Tooth dentin is very different from bone. The organic component of dentin (approximately 40%) makes most systems that will bond to bone and tooth enamel ineffective. Most current materials used for treatment of desensitization rely on materials that have been optimized for the bonding to bone and tooth enamel by their interaction with the inorganic components. As a result, even the most effective treatments are short lived. Therefore, there is a need in the dental field for a material that would chemically react with the surface of dentin and intimately bond to tooth structure, which would significantly reduce the reopening of dentin tubules due to contact with oral fluids.

It is therefore one object of the present invention to provide a composition that will accomplish at least the partial occlusion of dentinal tubules by chemical and physical interaction with the tooth structure.

It is a further object of the invention to provide a method of using a bioactive glass composition to reduce tooth hypersensitivity.

SUMMARY OF THE INVENTION

The present invention relates to a bioactive glass composition including particulate bioactive and biocompatible glass having the following composition by weight percentages:

| | |
| --- | --- |
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 | and a particle size range less than 90 $\mu$m, wherein the particulate bioactive and biocompatible glass includes an effective dentin tubule occluding amount of particles less than about 10 $\mu$m. The present invention also relates to a method of treating hypersensitive teeth and a method for occluding dentinal tubules.

DETAILED DESCRIPTION OF THE INVENTION

Figure 1:
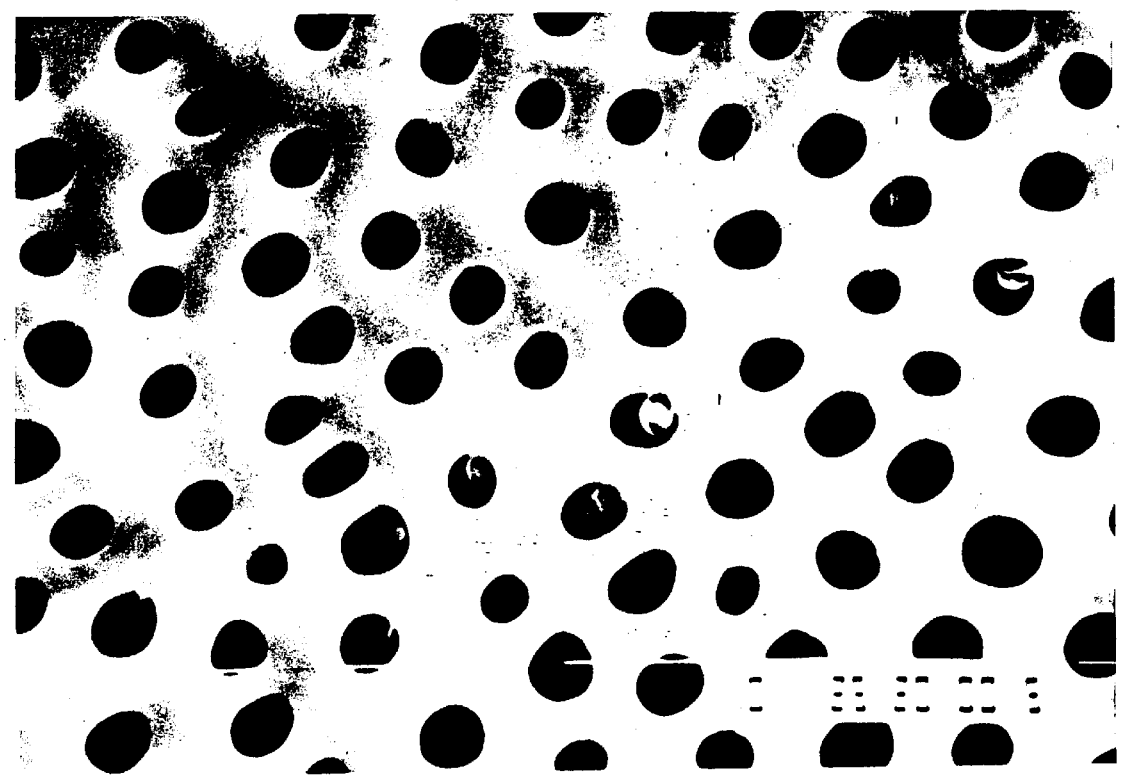
FIG. 1 depicts a dentin control surface that has been treated with 37% phosphoric acid for 30 seconds to remove any smear layer after sectioning and grinding to emulate clinical sensitivity. The surface has not been treated with bioactive glass in accordance with the present invention (2000× magnification).

The present invention provides a bioactive glass composition which is useful in treating tooth hypersensitivity. The composition of the present invention may be incorporated into a toothpaste, mouthwash, or be applied by a dentist as a paste. The composition is active in blocking patent dentinal tubules which is associated with tooth hypersensitivity, and will actually chemically bond to the tooth, reducing future hypersensitivity problems.

Surprisingly, in accordance with the present invention, it has been found that bioactive glasses of specified particle sizes are particularly useful in treating tooth hypersensitivity. One aspect of the present invention relates to a bioactive glass composition including particulate bioactive and biocompatible glass having the following composition by weight percentages:

| | |
|---|---|
| $SiO_2$ | 40–60 |
| CaO | 10–30 |
| $Na_2O$ | 10–35 |
| $P_2O_5$ | 2–8 |
| $CaF_2$ | 0–25 |
| $B_2O_3$ | 0–10 | and a particle size range less than 90 µm, wherein the particulate bioactive and biocompatible glass includes an effective dentin tubule occluding amount of particles less than about 10 µm. Another aspect of the present invention relates to a method of treating hypersensitive teeth and a method for occluding dentinal tubules.

Dentin tubules are approximately 1–2 µm in diameter with the dentin consisting of approximately 60% inorganic components and 40% organic composed mainly of collagen. As explained above, the occlusion of these tubules leads to a significant reduction in the amount of sensitivity. The compositions of the present invention will allow the silica component of the of the bioactive glass composition to chemically bond to the dentin surface resulting in reduction of tooth hypersensitivity. As the term "an effective dentin tubule occluding amount" is used herein, it is intended to mean an amount which provides for at least partial occlusion of dentinal tubules.

A bioactive glass in accordance with the present invention is a glass composition that will form a layer of hydroxycarbonate apatite in vitro when placed in a simulated body fluid. Bioactive glasses in accordance with the present invention are considered a class A bioactive material which will bond to both hard and soft tissue. Bioactive glasses with these properties provide a more efficacious material for interaction with the tooth structure. A biocompatible glass in accordance with the present invention is one that does not trigger an overwhelmingly adverse immune response.

Unlike earlier compositions, compositions in accordance with the present invention include very small particles, e.g. particles less than 10 µm. Preferably, some of these particles are actually small enough to fit inside the dentinal tubules (e.g. about 2 microns or less). In one embodiment of the present invention, some of the particles are small enough to fit inside the dentinal tubules (e.g. about 2 microns or less), and others are too large to fit inside the dentinal tubules (e.g. larger than about 2 microns).

Small sized particles in accordance with the present invention provide for mechanical and chemical occlusion of the tubules. The composition of the present invention actually provides a bioactive layer that will form a new structural layer which results in long lasting reduction of tooth hypersensitivity. This has been verified by the reformation of a hydroxycarbonate apatite layer on dentin surfaces after treatment with compositions in accordance with the present invention Fourier Transform Infrared spectrocopy (FTIR). Particles that are small enough to fit inside or rest on the opening of the tubules provide for actual physical occlusion of the tubules. Moreover, in contrast to particles larger than 90 microns, smaller particles in accordance with the present invention are more likely to adhere to the tubules or tooth surface because particles less than about 90 microns react quickly enough to chemically bond with dentin surfaces and tubules during the use of a toothpaste, gel or mouthwash including the composition of the present invention.

The inclusion of smaller sized particles in accordance with the present invention provides for many other surprising results. For example, there is an advantage associated with including small particles that are capable of bonding with tooth surfaces (e.g. less than about 90 microns) as well smaller particles (e.g. less than about 10 microns or preferably less than about 5 microns). When the larger of these particles adhere to tooth surfaces, they act as ionic reservoirs, capable of providing additional calcium and phosphorous to particles which have become attached to the inside or openings of dentinal tubules. This in turn provides for continued growth of the smaller of these particles which have lodged inside or over the openings of tubules and can result in complete occlusion of the tubules. This excess concentration of ions of calcium and phosphorous is necessary for continued reaction of the smaller of these particles to take place because the smaller particles quickly exhaust their ions as a result of their relatively high surface area. The larger of these particles will react and release their ions more slowly as a longer term effect. Furthermore, the larger of these particles will mechanically abrade the tooth surface opening the dentin tubules allowing small particles to enter and react with the dentin tubules.

Compositions in accordance with the present invention generally do not require time to set and provide for longer lasting occlusion of dentin tubules. Previous compositions of desensitizing agents washed away by mechanical abrasion caused by brushing, exposure to mild acids in food, salivary flow or other liquids which normally come in contact with the teeth. However, compositions in accordance with the present invention have been able to generally withstand significant agitation, rinsing with water and long term soaking in simulated saliva for five days. Moreover, the small particles of the present invention do not require a set time because they begin to chemically react and adhere to dentin surfaces as soon as they come into contact with these surfaces and fluids naturally present in the mouth. Although compositions in accordance with the present invention are effective with a single application, it is likely that multiple applications will be more efficacious.

Surprisingly, the relatively small bioactive particulate glass of the present invention does not generate a significant immune response. Moreover, it is generally not engulfed by macrophages and rendered inactive in this application.

In one embodiment in accordance with the present invention, the particles have a particle size of about 20 microns with about 30 percent of the particles less than 10 microns. In another embodiment in accordance with the present invention the particles have an average particle size of 10 microns with at least 25% smaller than 2 microns.

The compositions of the present invention may be formulated into toothpaste. In fact, the larger particles may replace the silica currently used, in toothpastes. The addition of fluoride in the glass composition will enhance and strengthen the tooth structure to make it more resistant to reoccurrence of hypersensitivity. In addition to direct application of the bioactive glass to the teeth, the bioactive glass composition of the present invention can also be applied in a saline or distilled water based medium. The compositions of the present invention may also be formulated into mouthwash, gel or they may be applied by a dentist as a paste.

EXAMPLES

Figure 2:
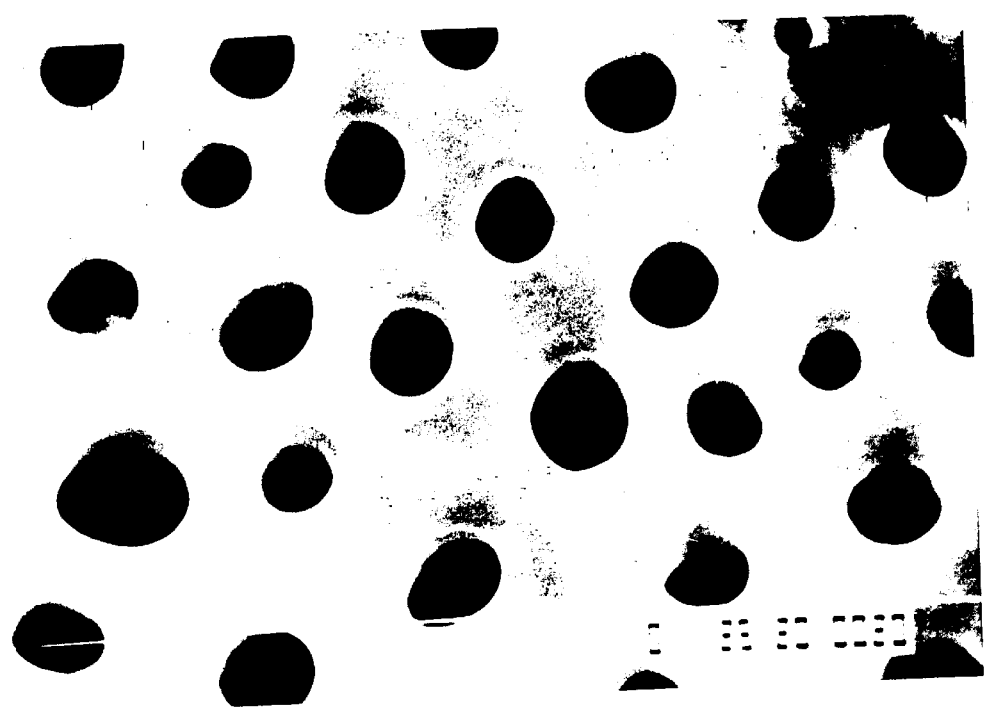
FIG. 2 depicts a dentin control surface that has been treated with 37% Phosphoric acid for 30 seconds to remove any smear layer after sectioning and grinding to emulate clinical sensitivity. The surface has not been treated with bioactive glass in accordance with the present invention (3000× magnification).
Figure 3:
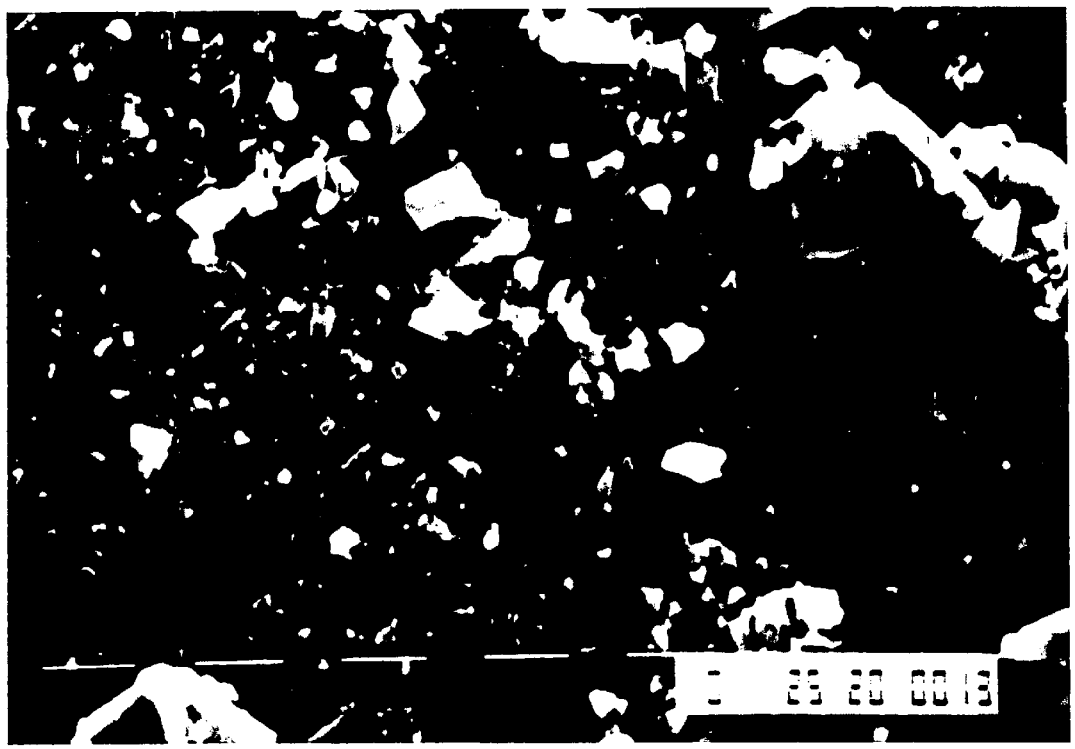
FIG. 3 depicts a dentin surface that has been treated with an acid etch and treated with a bioactive glass composition in accordance with the present invention in water and glycerin for 2 minutes (Particle size range submicron to 90 µm, 1000× magnification).
Figure 4:
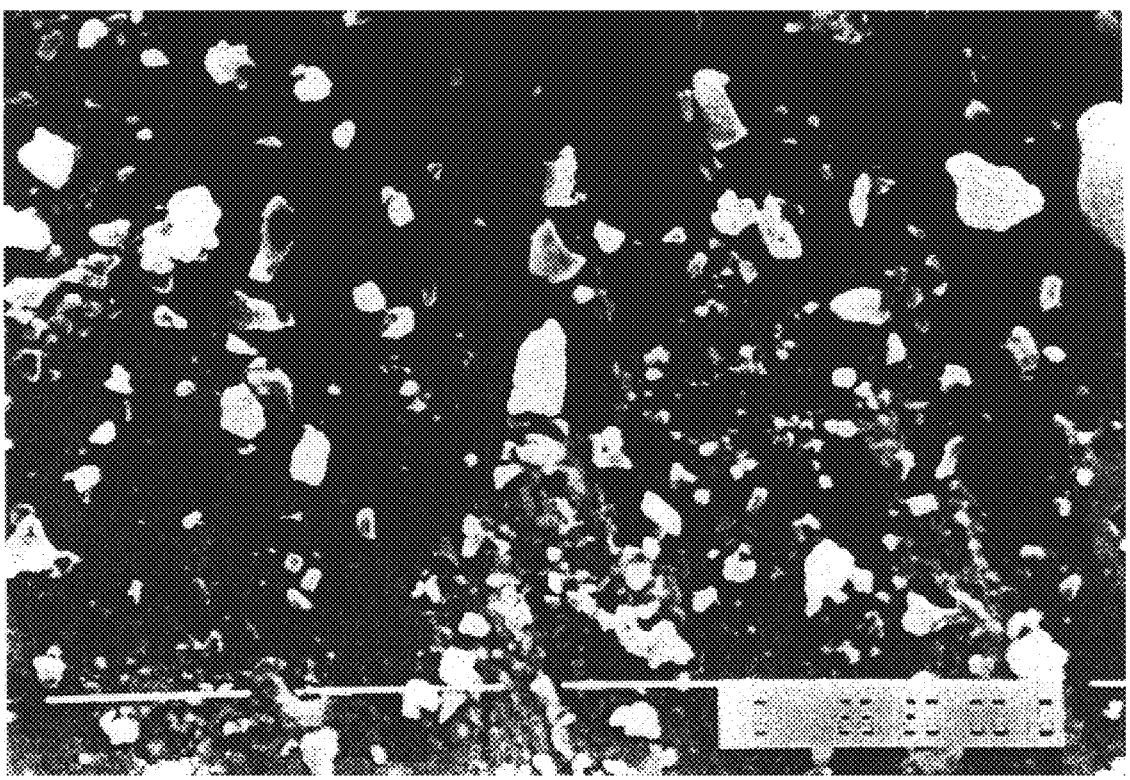
FIG. 4 depicts a dentin surface that has been acid etched and subsequently treated with a bioactive glass composition in accordance with the present invention in water and glycerin for 2 minutes. The surfaces were subsequently agitated and water rinsed for 2 minutes (Particle size range submicron to 20 µm, 2000× magnification).
Figure 5:
FIG. 5 depicts a dentin surface that has been acid etched and subsequently treated with a bioactive glass composition in accordance with the present invention and placed in water for 3 days. There was no subsequent agitation, but the surface was water rinsed for 2 minutes (Particle size range submicron to 90 µm, 2000× magnification).
Figure 6:
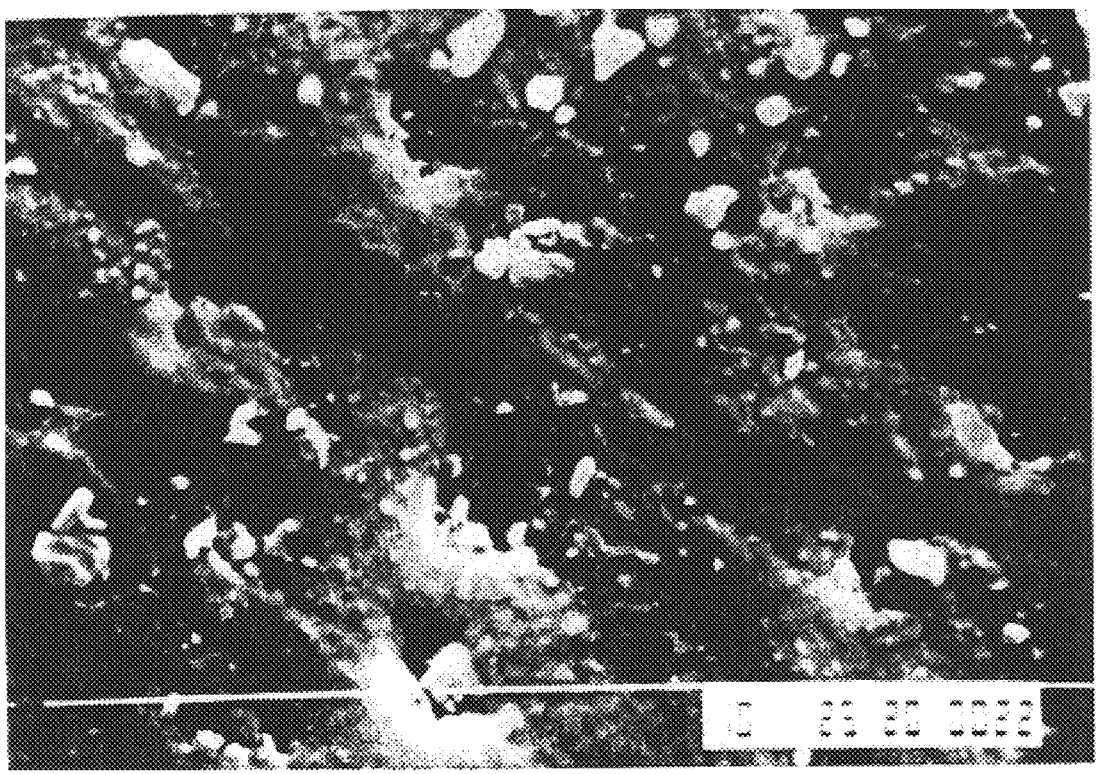
FIG. 6 depicts a dentin surface that has been acid etched and subsequently treated with a bioactive glass composition in accordance with the present invention in water and toothpaste for 2 minutes with agitation and a subsequent 2 minute water rinse (Particle size range submicron to 3 µm, 3000× magnification).
Figure 7:
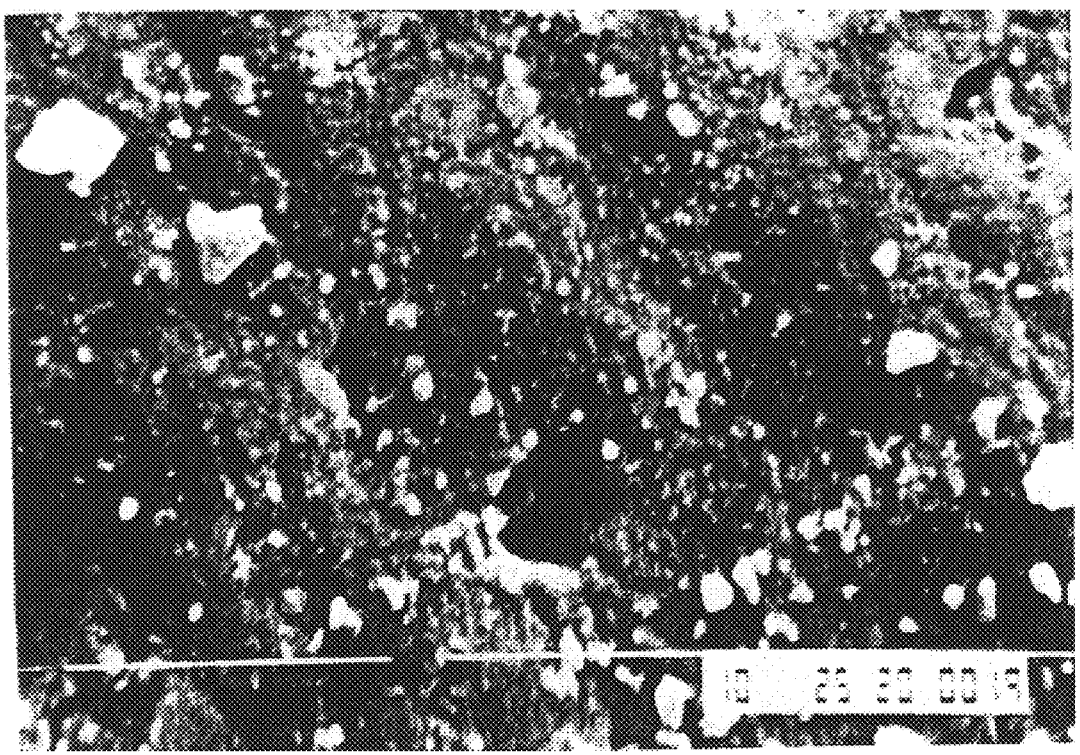
FIG. 7 depicts a dentin surface that has been acid etched and treated with a bioactive glass composition in accordance with the present invention in water and toothpaste for 2 minutes with agitation and water rinse for 2 minutes (Particle size range submicron to 3 µm, 3500× magnification).

The following working examples are non-limiting:

in vitro experiments were performed using a standardized slab of human tooth dentin from extracted teeth. These discs were cut from the extracted teeth using an Isomet diamond saw (Buchler Ltd.). The discs were 1.0 mm thick and the size of the tooth. The occlusal surfaces were ground on a series of wet silicon-carbide papers ranging from 320 to 600 grit. This was done to standardize the test surfaces. The surfaces were treated with 37% phosphoric acid for 60 seconds to remove the smear layer created during the grinding process and open and enlarge all the dentin tubules (See FIGS. 1 and 2). The surface was rinsed with distilled water for 20 seconds and dried with a stream of oil free air. Each slab was split in half and the experimental material placed on one-half of the specimen as described in the examples. An untreated slab with open and enlarged tubules is shown in FIGS. 1 and 2.

Scanning electron microscopy was performed on the slab surface in each group. The slabs were mounted on scanning electron microscope stubs using sliver paste. All specimens were vacuum dried, sputter coated and examined in a JEOL-T200 scanning electron microscope.

Example 1

The starting product was a mixture containing (% by weight)

| | |
|---|---|
| $SiO_2$ | 45 |
| CaO | 24.5 |
| $Na_2O$ | 24.5 |
| $P_2O_5$ | 6 |

The mixture was melted in a covered platinum crucible at 1350° C. for 2 hours to achieve homogenization. The mixture was later quenched in deionized water at 0° C. Fritted glass was placed in an appropriate milling apparatus including ball mill, impact mill. The glass is milled for 2 hours and separated into appropriate size ranges.

The particle size range less than 90 $\mu$m was obtained using this process and confirmed by scanning electron microscopy and laser light scattering technique (Coulter LS 100). These mixtures were placed on the dentin slabs previously described.

The exposure times to the dentin varied between two minutes with scrubbing to 3 days with no agitation. The occlusion of the tubules is depicted in FIGS. 3–7. Visible in FIGS. 3–7 are total and partial occlusion of the dentin tubules with multiple size of small (1–5 $\mu$m) particles present. In addition, larger particles that are visible that will act as reservoirs for the chemical composition. Early formation of hydroxyapatite crystals is beginning on the dentin surface confirmed by FTIR.

Example 2

Figure 8:
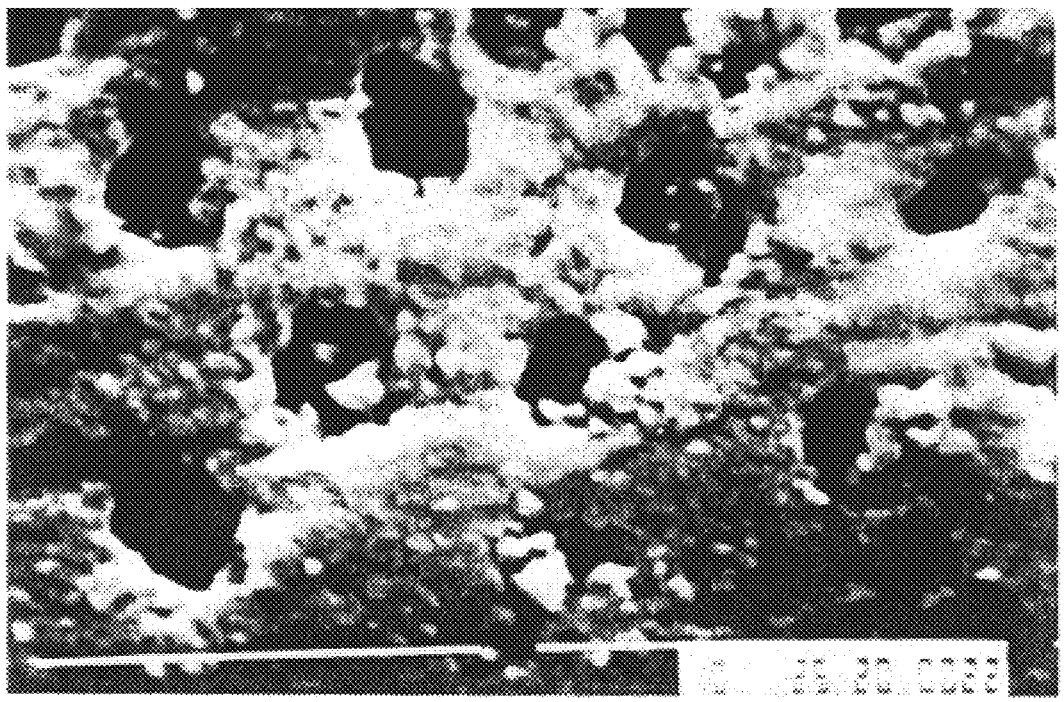
FIGS. 8 and 9 depict a dentin surface which has been acid etched with phosphoric acid, treated with a bioactive glass for 2 minutes and immersed in a phosphate buffered saline for 5 days (Particle size range submicron).
Figure 9:
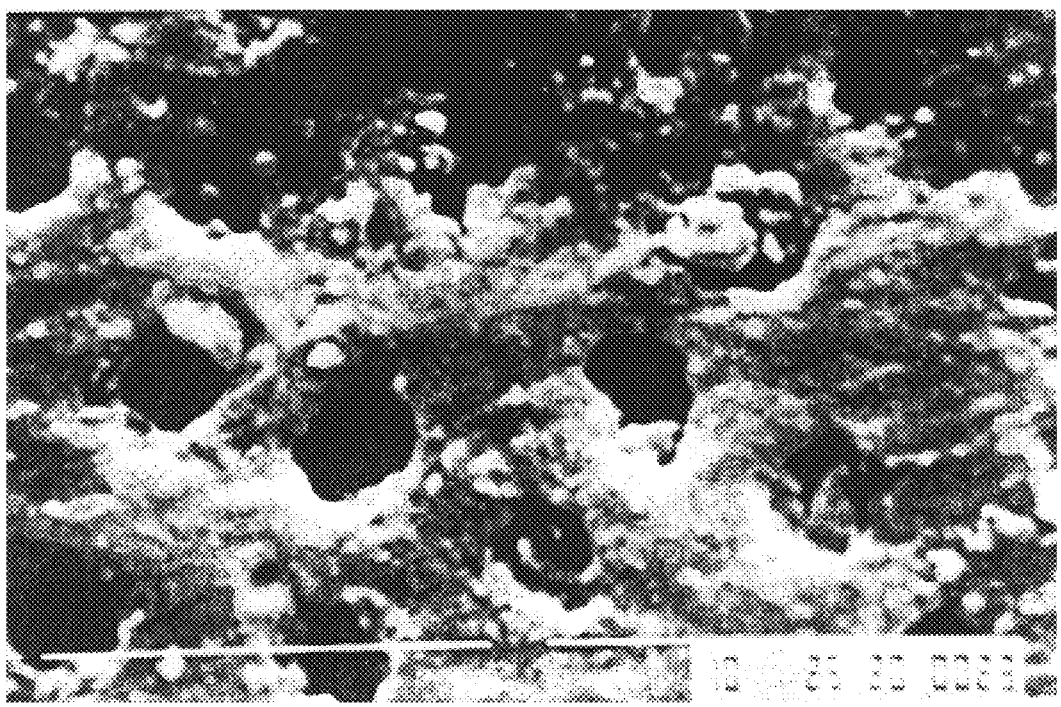

FIGS. 8 and 9 indicate the results obtainable by using submicron particles made in accordance with Example 1. With the lack of large particles for reservoir activity, there was less complete regeneration as confirmed by FTIR.

Other Examples

The composition of the starting product for the following examples was the same as Example 1 except the level of $SiO_2$ was 45%, 55%, and 60%. Also, the method of preparation was different. The mixture was melted in a covered platinum crucible at 1350° C. for 2 hours to achieve homogenization. The mixture was poured into a slab, allowed to cool to room temperature and crushed with a hammer. Crushed glass fractions were then separated by sieving through a standard screen. Fractions were then separated and retained.

The particle size range less than 90 $\mu$m was obtained using this process and confirmed by scanning electron microscopy and laser light scattering technique (Coulter LS 100). These mixtures were placed on the dentin slabs previously described.

Samples containing 45%, 55%, and 60% $SiO_2$ were utilized in the preparations with the same results seen in Example 1. Again, the key to these data was the presence of the sized range of particles. Present in these examples are ranges up to 60% silica with a size range in particles from submicron to 90 micron showing like reactions to Example 1 on the dentin surfaces.

Although the present invention has been described in one or more embodiments, this description is not intended to in any way limit the scope of the claims.

We claim:

1. A bioactive glass composition comprising particulate bioactive and biocompatible glass having the following approximate composition by weight percentage:

| | |
|---|---|
| $SiO_2$ | 45 |
| CaO | 24.5 |
| $Na_2O$ | 24.5 |
| $P_2O_5$ | 6 | including particles less than 90 µm, wherein the particulate bioactive and biocompatible glass includes an effective dentin tubule occluding amount of particles less than about 2 µm.

2. A bioactive silica glass composition comprising particulate bioactive and biocompatable glass with a silica content of at least 40% and an effective dentin tubule occluding amount of particles less than about 5 microns wherein said bioactive glass comprises an effective amount of Ca and P to form hydroxyapatite in vivo.

* * * * *